United States Patent
Niwa et al.

(10) Patent No.: US 8,652,845 B2
(45) Date of Patent: Feb. 18, 2014

(54) METHOD FOR PRODUCING MESODERMAL CELLS BY CULTURING UNDER ADHERENT CONDITIONS AND WITHOUT CO-CULTURE WITH CELLS FROM A DIFFERENT SPECIES IN A SERUM-FREE MEDIUM

(75) Inventors: Akira Niwa, Kyoto (JP); Tatsutoshi Nakahata, Kyoto (JP); Toshio Heike, Kyoto (JP)

(73) Assignee: Kyoto University, Kyoto (JP)

( * ) Notice: Subject to any disclaimer, the term of this patent is extended or adjusted under 35 U.S.C. 154(b) by 0 days.

(21) Appl. No.: 13/635,679

(22) PCT Filed: Mar. 18, 2011

(86) PCT No.: PCT/JP2011/057503
§ 371 (c)(1),
(2), (4) Date: Sep. 17, 2012

(87) PCT Pub. No.: WO2011/115308
PCT Pub. Date: Sep. 22, 2011

(65) Prior Publication Data
US 2013/0011924 A1  Jan. 10, 2013

Related U.S. Application Data

(60) Provisional application No. 61/315,170, filed on Mar. 18, 2010.

(51) Int. Cl.
*C12N 5/095* (2010.01)
(52) U.S. Cl.
USPC ............ 435/377; 435/373; 435/402; 435/405
(58) Field of Classification Search
None
See application file for complete search history.

(56) References Cited

U.S. PATENT DOCUMENTS

2005/0158855 A1*   7/2005   Carpenter et al. ............ 435/368
2005/0214939 A1*   9/2005   Gold et al. .................... 435/366
2010/0093053 A1*   4/2010   Oh et al. ....................... 435/176

FOREIGN PATENT DOCUMENTS

| WO | WO 2008/056779 A1 | 5/2005 |
| WO | WO 2007/120811 A2 | 10/2007 |
| WO | WO 2009/120891 A2 | 10/2009 |
| WO | WO 2010/008100 A1 | 1/2010 |

OTHER PUBLICATIONS

Yange et al. "Human cardiovascular progenitor cells develop from a KDR1 embryonic-stem-cell-derived population" Nature 453, Issue 22, May 2008 pp. 524-529.*
Messina et al. "Isolation and Expansion of Adult Cardiac Stem Cells From Human and Murine Heart" Circ Res. 2004; vol. 95 pp. 911-921.*
Chadwick, K., et al., "Cytokines and BMP-4 Promote Hematopoietic Differentiation of Human Embryonic Stem Cells," Blood 102(3):906-915, 2003.
International Search Report dated Jun. 28, 2011 issued in connection with PCT/JP2011/057503.
Niwa, A., et al., Orderly Hematopoietic Development of Induced Pluripotent Stem Cells Via Flk-1(+) Hemoangiogenic Progenitors, J. Cell. Physiol. 221(1):367-377, 2009.
Niwa, A., et al., "A Novel Serum-Free Monolayer Culture for Orderly Hematopoietic Differentiation of Human Pluripotent Cells via Mesodermal Progenitors," PLoS ONE 6(7):1-11, 2011.
Saeki, K., et al., "A Feeder-Free and Efficient Production of Functional Neutrophils From Human Embryonic Stem Cells," Stem Cells 27(1):59-67, 2009.
Vijayaragavan, K., "Noncanonical Wnt Signaling Orchestrates Early Development Events Toward Hematopoietic Cell Fate From Human Embryonic Stem Cells," Cell Stem Cell 4(3):248-262, 2009.

\* cited by examiner

*Primary Examiner* — Deborah Crouch
*Assistant Examiner* — Titilayo Moloye
(74) *Attorney, Agent, or Firm* — Knobbe Martens Olson & Bear LLP

(57) ABSTRACT

The present invention provides a method for inducing differentiation of pluripotent stem cells into mesodermal cells, comprising the step of culturing pluripotent stem cells in a serum-free medium without forming an embryoid body and without coculturing with cells from a different species.

9 Claims, 14 Drawing Sheets

A

Cocktail A

Ery

Mk

Cocktail B

MPO hHb

IC

CD41

B

Cocktail A

Cocktail B

METHOD FOR PRODUCING MESODERMAL CELLS BY CULTURING UNDER ADHERENT CONDITIONS AND WITHOUT CO-CULTURE WITH CELLS FROM A DIFFERENT SPECIES IN A SERUM-FREE MEDIUM

BACKGROUND ART

Cells having pluripotency, such as embryonic stem cells (ES cells), and induced pluripotent stem cells (iPS cells) obtained by introducing undifferentiated cell-specific genes into somatic cells have been reported so far (U.S. Pat. No. 5,843,780 and WO 2007/069666). Therefore, recent interest has focused on regenerative medicine wherein cells obtained by inducing differentiation of these pluripotent stem cells are transplanted, and preparation of a pathologic model in vitro. As methods for preparing blood cells from embryonic stem cells, the method by formation of an embryoid body and addition of cytokines (Chadwick et al. Blood 2003, 102: 906-15; Vijayaragavan et al. Cell Stem Cell 2009, 4: 248-62; Saeki et al. Stem Cells 2009, 27: 59-67) and the method by coculture with stromal cells derived from a different species (Niwa A et al. J Cell Physiol. 2009 November; 221(2):367-77) have been employed so far. However, in the method by formation of an embryoid body, only a part of the cells are differentiated into blood cells, while many other cells are induced to differentiate into other types of cells. Further, for constantly preparing the same model in preparation of a pathologic model, the culture medium to be used preferably has only a restricted number of components in order to reduce uncertainties as much as possible.

However, there has been no report on mesoderm, hematopoietic stem cells or hematopoietic progenitor cells produced from pluripotent stem cells by a method wherein an embryoid body is not formed and coculturing with cells from a different species is not carried out and a culture medium having only a restricted number of components is used.

SUMMARY OF THE INVENTION

The present invention aims to efficiently produce mesoderm, and hematopoietic stem cells or hematopoietic progenitor cells from pluripotent stem cells. Therefore, an object of the present invention is to provide culture conditions under which human pluripotent stem cells, especially human induced pluripotent stem cells are induced to differentiate into mesoderm, and hematopoietic stem cells or hematopoietic progenitor cells.

In order to solve the above objects, the inventors of the present invention prepared mesodermal cells by subjecting pluripotent stem cells solely to adherent culture in a serum-free culture medium supplemented with cytokines such as BMP4 and VEGF. Subsequently, by adding hematopoietic factors to these mesodermal cells and continuing the culture, differentiation into hematopoietic stem cells or hematopoietic progenitor cells was induced.

From the above results, the inventors of the present invention succeeded in efficient production of hematopoietic stem cells or hematopoietic progenitor cells by culturing pluripotent stem cells under appropriate culture conditions and inducing differentiation of mesodermal cells under limited conditions, thereby completed the present invention.

It is an aspect of the present invention to provide a method for producing mesodermal cells, comprising the step of culturing pluripotent stem cells in a serum-free medium without forming an embryoid body and without coculturing with cells from a different species.

It is another aspect of the present invention to provide the method as described above, wherein cytokines including BMP4, and VEGF are added to the serum-free medium.

It is another aspect of the present invention to provide the method as described above, wherein the method for producing mesodermal cells comprises the following steps:
(1) pluripotent stem cells are cultured in the serum-free medium comprising BMP4; and
(2) cells obtained in step (1) are cultured in the serum-free medium comprising VEGF.

It is another aspect of the present invention to provide the method as described above, wherein the medium at step (2) further comprises SCF.

It is another aspect of the present invention to provide the method as described above, wherein the medium at step (1) and (2) further comprises Wnt3a.

It is another aspect of the present invention to provide the method as described above, wherein the step (1) is performed for 4 days.

It is another aspect of the present invention to provide the method as described above, wherein the step (2) is performed for 2 days.

It is another aspect of the present invention to provide the method as described above, wherein the culture is performed on a Matrigel™-coating dish.

It is another aspect of the present invention to provide the method as described above, wherein the method for producing mesodermal cells comprises the following steps:
(i) pluripotent stem cells are cultured in the presence of only BMP4;
(ii) pluripotent stem cells are cultured in the presence of BMP4 and Wnt3a; and
(iii) pluripotent stem cells are cultured in the presence of VEGF and Wnt3a.

It is another aspect of the present invention to provide the method as described above, wherein the step (i) is performed for 1 day.

It is another aspect of the present invention to provide the method as described above, wherein the step (ii) is performed for 3 days.

It is another aspect of the present invention to provide the method as described above, wherein the step (iii) is performed for 2 days.

It is another aspect of the present invention to provide the method as described above, wherein the concentration of BMP4 in the medium is 10 ng/mL to 40 ng/mL.

It is another aspect of the present invention to provide the method as described above, wherein the concentration of Wnt3a in the medium is 10 ng/mL to 20 ng/mL.

It is another aspect of the present invention to provide the method as described above, wherein the concentration of VEGF in the medium is 10 ng/mL to 20 ng/mL.

It is another aspect of the present invention to provide the method as described above, wherein said mesodermal cells contain KDR-positive and CD34-positive cells.

It is another aspect of the present invention to provide a method for producing hematopoietic stem cells, hematopoietic progenitor cells, myeloid cells, megakaryocytes, erythrocytes and/or neutrophils, comprising
a) producing mesodermal cells by the method according to claim 1, and
b) producing hematopoietic stem cells, hematopoietic progenitor cells, myeloid cells, megakaryocytes, erythrocytes and/or neutrophils from the mesodermal cells.

It is another aspect of the present invention to provide the method as described above, wherein the step b) is performed by culturing the mesodermal cells obtained in step a) in the presence of a hematopoietic factor(s).

It is another aspect of the present invention to provide the method as described above, wherein said hematopoietic factors are selected from the group consisting of SCF, TPO, EPO, IL-3, Flt3-ligand, FP-6 and G-CSF.

It is another aspect of the present invention to provide the method as described above, wherein said hematopoietic factors are SCF, TPO, IL-3, Flt3-ligand and G-CSF.

It is another aspect of the present invention to provide the method as described above, wherein said hematopoietic factors are SCF, TPO, IL-3, FP-6 and EPO.

It is another aspect of the present invention to provide the method as described above, wherein the step b) is performed for 9 days or more.

BRIEF DESCRIPTION OF THE DRAWINGS

In FIG. 1, B shows immunostained images (photograph) of the respective marker proteins on Day 0 (ES cells), Day 4 (Step A) and Day 6 (Step B). Here, "IC" indicates images obtained by staining with only DAPI to provide a control.

In FIG. 6, B shows the results of flow cytometry for detection of expression of the respective marker proteins in the cells cultured for 24 days after replacement of the culture medium with the myeloid inducing factor cocktail (Cocktail A) or the megakaryoblast/erythroblast inducing factor cocktail (Cocktail B), which replacement was carried out on Day 6 after the beginning of the differentiation induction.

In FIG. 11, B shows the numbers of the respective colony-forming units on the respective days after the beginning of the differentiation induction.

DESCRIPTION OF THE PREFERRED EMBODIMENTS

Figure 1:
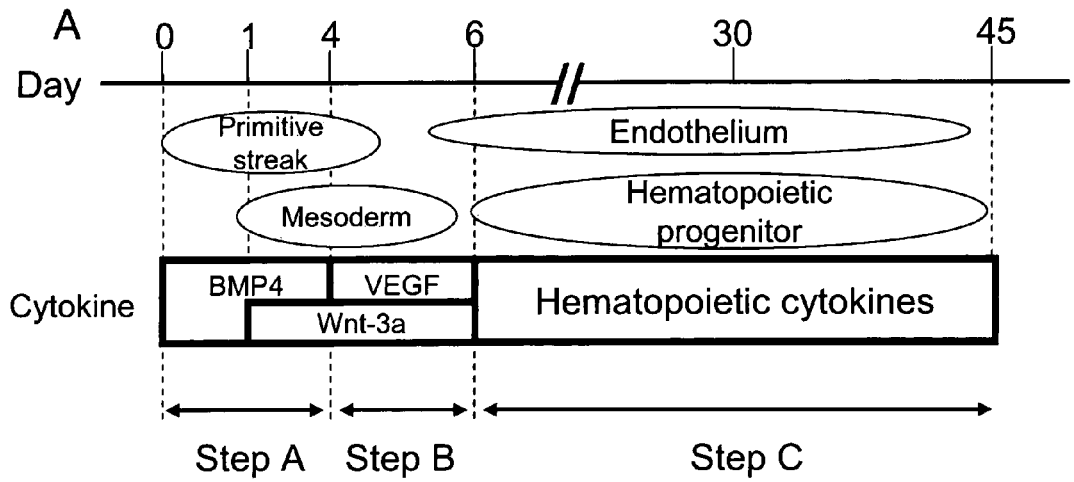
In FIG. 1, A shows a scheme of differentiation induction into hematopoietic stem cells and/or hematopoietic progenitor cells. The process is divided into the primitive streak-inducing step (Step A), the mesoderm-inducing step (Step B) and the hematopoietic stem cell and/or hematopoietic progenitor cell-inducing step (Step C).
Figure 1:
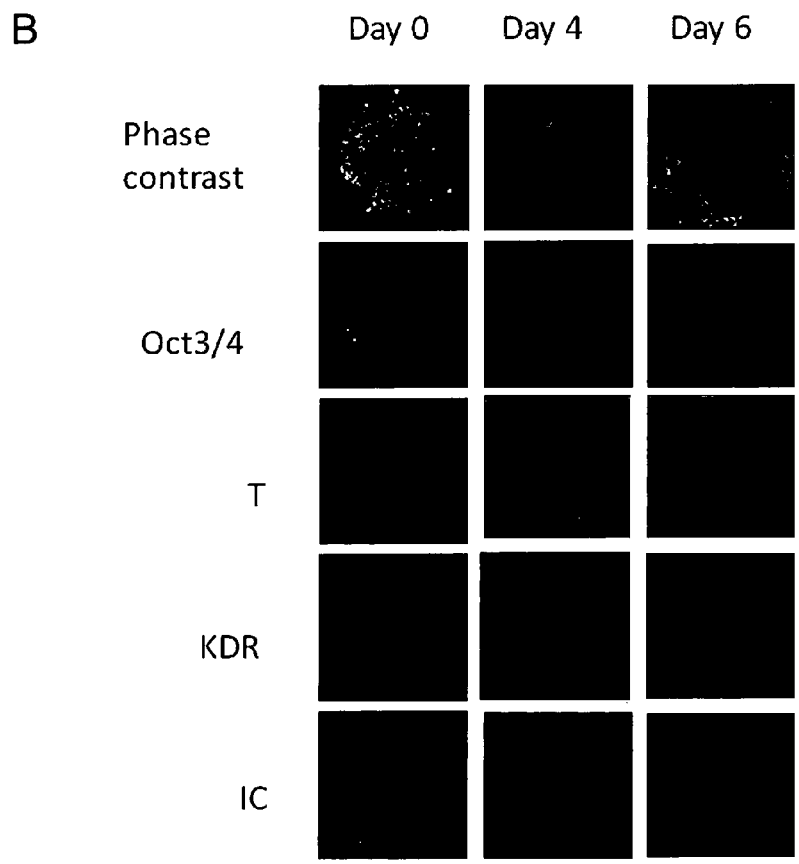

The present invention will now be described in detail.

As described above, the present invention relates to a method for producing mesodermal cells from pluripotent stem cells, which method comprises the step of culturing pluripotent stem cells in a serum-free medium without forming an embryoid body and without coculturing with cells from a different species.

<Pluripotent Stem Cells>

The pluripotent stem cells which can be used in the present invention are stem cells having pluripotency which enables the cells to differentiate into any cells existing in the living body, which pluripotent stem cells also have growth ability. Examples of the pluripotent stem cells include, but are not limited to, embryonic stem (ES) cells, embryonic stem cells derived from a cloned embryo obtained by nuclear transfer ("ntES cells"), germline stem cells ("GS cells"), embryonic germ cells ("EG cells") and induced pluripotent stem (iPS) cells. Preferred examples of the pluripotent stem cells include ES cells, ntES cells and iPS cells.

(A) Embryonic Stem Cells

ES cells are stem cells established from the inner cell mass of an early embryo (for example, blastocyst) of a mammal such as human or mouse, which cells have pluripotency and growth ability by self-renewal.

ES cells are embryo-derived stem cells originated from the inner cell mass of a blastocyst which is an embryo formed following the 8-cell stage and the morula stage of a fertilized egg, and ES cells have ability to differentiate into any cells constituting an adult, that is, the so called pluripotency of differentiation, and growth ability by self-renewal. ES cells was discovered in mouse in 1981 (M. J. Evans and M. H. Kaufman (1981), Nature 292:154-156), and this was followed by establishment of ES cell lines of primates such as human and monkey (J. A. Thomson et al. (1999), Science 282:1145-1147; J. A. Thomson et al. (1995), Proc. Natl. Acad. Sci. USA, 92:7844-7848; J. A. Thomson et al. (1996), Biol. Reprod., 55:254-259; J. A. Thomson and V. S. Marshall (1998), Curr. Top. Dev. Biol., 38:133-165).

ES cells can be established by removing the inner cell mass from the blastocyst of a fertilized egg of the subject animal, followed by culturing the inner cell mass on fibroblasts as feeders. The cells can be maintained by subculturing using a culture medium supplemented with substances such as leukemia inhibitory factor (LIF) and basic fibroblast growth factor (bFGF). Methods of establishment and maintenance of human and monkey ES cells are described in, for example, H. Suemori et al. (2006), Biochem. Biophys. Res. Commun., 345:926-932; M. Ueno et al. (2006), Proc. Natl. Acad. Sci. USA, 103:9554-9559; H. Suemori et al. (2001), Dev. Dyn., 222:273-279; and H. Kawasaki et al. (2002), Proc. Natl. Acad. Sci. USA, 99:1580-1585.

In terms of the culture medium for preparation of ES cells, human ES cells can be maintained, for example, using DMEM/F-12 medium supplemented with 0.1 mM 2-mercaptoethanol, 0.1 mM non-essential amino acids, 2 mM L-glutamic acid, 20% KSR and 4 ng/ml β-FGF, at 37° C. in 2% $CO_2$/98% air under a moist atmosphere (O. Fumitaka et al. (2008), Nat. Biotechnol., 26:215-224). Further, ES cells need to be subcultured every 3 to 4 days, and the subculture can be carried out using 0.25% trypsin and 0.1 mg/ml collagenase IV in PBS supplemented with 1 mM $CaCl_2$ and 20% KSR.

Selection of ES cells can be generally carried out by the Real-Time PCR method using expression of gene markers such as alkaline phosphatase, Oct-3/4 and Nanog as indices. In particular, for selection of human ES cells, expression of gene markers such as OCT-3/4, NANOG and ECAD can be used as indices (E. Kroon et al. (2008), Nat. Biotechnol., 26:443-452).

Human ES cell lines such as KhES-1, KhES-2 and KhES-3 can be obtained from Institute for Frontier Medical Sciences, Kyoto University (Kyoto, Japan).

(B) Germline Stem Cells

Germline stem cells are pluripotent stem cells derived from testis, and play a role as the origin for spermatogenesis. Similarly to ES cells, these cells can be induced to differentiate into various series of cells, and, for example, have a property to enable preparation of a chimeric mouse by transplanting the cells to a mouse blastocyst (M. Kanatsu-Shinohara et al. (2003) Biol. Reprod., 69:612-616; K. Shinohara et al. (2004), Cell, 119:1001-1012). Germline stem cells are capable of self-renewal in a culture medium containing glial cell line-derived neurotrophic factor (GDNF), and, by repeating subculture under the same culture conditions as those for ES cells, germline stem cells can be obtained (Masanori Takehashi et al. (2008), Experimental Medicine, 26(5) (extra edition):41-46, Yodosha (Tokyo, Japan)).

(C) Embryonic Germ Cells

Embryonic germ cells are established from fetal primordial germ cells and have pluripotency similarly to ES cells. They can be established by culturing primordial germ cells in the presence of substances such as LIF, bFGF and stem cell factor (Y. Matsui et al. (1992), Cell, 70:841-847; J. L. Resnick et al. (1992), Nature, 359:550-551).

(D) Induced Pluripotent Stem Cells

Induced pluripotent stem (iPS) cells can be prepared by introducing certain specific reprogramming factors to somatic cells, which reprogramming factors are in the forms of DNAs or proteins. iPS cells are somatic cell-derived artificial stem cells having properties almost equivalent to those of ES cells, such as pluripotency of differentiation and growth ability by self-renewal (K. Takahashi and S. Yamanaka (2006) Cell, 126:663-676; K. Takahashi et al. (2007), Cell, 131:861-872; J. Yu et al. (2007), Science, 318:1917-1920; Nakagawa, M. et al., Nat. Biotechnol. 26:101-106 (2008); WO 2007/069666). The reprogramming factors are not restricted as long as these are genes specifically expressed in ES cells, or genes playing important roles in maintenance of the undifferentiated state of ES cells, or gene products thereof. Examples of the combination of the reprogramming factors include OCT3/4, SOX2 and KLF4; OCT3/4, KLF4 and C-MYC; OCT3/4, SOX2, KLF4 and C-MYC; OCT3/4 and SOX2; OCT3/4, SOX2 and NANOG; OCT3/4, SOX2 and LIN28; and OCT3/4 and KLF4.

These factors may be introduced into somatic cells in the form of protein by a method such as lipofection, linking with a cell-permeable peptide, or microinjection, or in the form of DNA by a method such as usage of a vector including virus, plasmid and artificial chromosome vectors, lipofection, usage of liposome, or microinjection. Examples of the virus vectors include retrovirus vectors, lentivirus vectors (these are described in Cell, 126, pp. 663-676, 2006; Cell, 131, pp. 861-872, 2007; and Science, 318, pp. 1917-1920, 2007), adenovirus vectors (Science, 322, 945-949, 2008), adeno-associated virus vectors, and Sendai virus vectors. Examples of the artificial chromosome vectors include human artificial chromosome (HAC), yeast artificial chromosome (YAC), and bacterial artificial chromosome (BAC, PAC). Examples of the plasmids include plasmids for mammalian cells (Science, 322:949-953, 2008). The vectors may contain a regulatory sequence(s) such as a promoter, enhancer, ribosome binding sequence, terminator and/or polyadenylation site; and, as required, a sequence of a selection marker such as a drug resistance gene (e.g., kanamycin-resistant gene, ampicillin-resistant gene or puromycin-resistant gene), thymidine kinase gene or diphtheria toxin gene; and a gene sequence of a reporter such as the green-fluorescent protein (GFP), β-glucuronidase (GUS) or FLAG. Further, in order to remove, after introduction of the above vector into somatic cells, the genes encoding the reprogramming factors, or both the promoters and the genes encoding the reprogramming factors linked thereto, the vector may have loxP sequences in the upstream and the downstream of these sequences.

For enhancing the induction efficiency upon the reprogramming, histone deacetylase (HDAC) inhibitors [for example, low molecular inhibitors such as valproic acid (VPA)(Nat. Biotechnol., 26(7): 795-797 (2008)), trichostatin A, sodium butyrate, MC 1293 and M344; and nucleic acid-type expression inhibitors such as siRNAs and shRNAs against HDAC (e.g., HDAC1 siRNA Smartpool® (Millipore) and HuSH 29 mer shRNA Constructs against HDAC1 (Origene))], DNA methyltransferase inhibitors (e.g., 5'-azacytidine) (Nat. Biotechnol., 26(7): 795-797 (2008)), G9a histone methyltransferase inhibitors [for example, low molecular inhibitors such as BIX-01294 (Cell Stem Cell, 2: 525-528 (2008)); and nucleic acid-type expression inhibitors such as siRNAs and shRNAs against G9a (e.g., G9a siRNA (human) (Santa Cruz Biotechnology))], L-channel calcium agonists (e.g., Bayk8644) (Cell Stem Cell, 3, 568-574 (2008)), p53 inhibitors [e.g., siRNAs and shRNAs against p53 (Cell Stem Cell, 3, 475-479 (2008))], UTF1 (Cell Stem Cell, 3, 475-479 (2008)), Wnt Signaling (e.g., soluble Wnt3a) (Cell Stem Cell, 3, 132-135 (2008)), 2i/LIF (2i is an inhibitor of mitogen-activated protein kinase signaling and glycogen synthase kinase-3, PloS Biology, 6(10), 2237-2247 (2008)), miRNAs such as miR-291-3p, miR-294 and miR-295 (R. L. Judson et al., Nat. Biotech., 27:459-461 (2009)), and the like may be used in addition to the above-described factors.

Examples of the culture medium for induction of the iPS cells include (1) DMEM, DMEM/F12 and DME supplemented with 10 to 15% FBS (these media may further contain LIF, penicillin/streptomycin, puromycin, L-glutamine, non-essential amino acids, β-mercaptoethanol and/or the like, as appropriate); (2) culture media for ES cells containing bFGF or SCF, for example, culture media for mouse ES cells (e.g., TX-WES medium, Thromb-X) and culture media for primate ES cells (e.g., culture medium for primate (human and monkey) ES cells, ReproCELL Inc., Kyoto, Japan).

Examples of the culture method include a method wherein somatic cells and reprogramming factors (DNAs or proteins) are brought into contact with each other at 37° C. in the presence of 5% $CO_2$ on DMEM or DMEM/F12 medium supplemented with 10% FBS, and the cells are cultured for 4 to 7 days, followed by plating the cells on feeder cells (e.g., mitomycin C-treated STO cells, SNL cells or the like), starting culture in a culture medium for primate ES cells supplemented with bFGF about 10 days after the contact between the somatic cells and the reprogramming factors, thereby allowing iPS-like colonies to appear about 30 to about 45 days after the contact, or later.

As an alternative culture method, the culture can be carried out at 37° C. in the presence of 5% $CO_2$ on feeder cells (e.g., mitomycin C-treated STO cells, SNL cells or the like) in DMEM culture medium supplemented with 10% FBS (this may further contain LIF, penicillin/streptomycin, puromycin, L-glutamine, non-essential amino acids, β-mercaptoethanol and/or the like, as appropriate), thereby allowing ES-like colonies to appear about 25 to about 30 days thereafter, or later.

During the above culturing period, the culture medium is replaced with fresh culture medium once every day from Day 2 of the culture. The number of the somatic cells used for nuclear reprogramming is not restricted, and usually within the range of about $5\times10^3$ to about $5\times10^6$ cells per 100 $cm^2$ culture dish.

In cases where a gene including a drug resistance gene is used as a marker gene, cells expressing the marker gene can be selected by culturing the cells in a culture medium (selection medium) containing the corresponding drug. Cells expressing a marker gene can be detected by observation under a fluorescence microscope in cases where the marker gene is the gene of a fluorescent protein; by adding a luminescent substrate in cases where the marker gene is the gene of luciferase; or by adding a coloring substrate in cases where the marker gene is the gene of a coloring enzyme.

The term "somatic cells" used in the present specification means any animal cells (preferably cells of mammals including human) excluding germ-line cells and totipotent cells such as eggs, oocytes and ES cells. Examples of the somatic cells include, but are not limited to, any of fetal somatic cells, neonatal somatic cells, and mature, healthy or diseased, somatic cells, as well as any of primary cultured cells, subcultured cells and established cell lines, and further, tissue stem cells and tissue progenitor cells. More particular examples of the somatic cells include, but are not limited to, (1) tissue stem cells (somatic stem cells) such as neural stem cells, hematopoietic stem cells, mesenchymal stem cells and dental pulp stem cells; (2) tissue progenitor cells; and (3) differentiated cells such as lymphocytes, epithelial cells, endothelial cells, muscle cells, fibroblasts (skin cells and the like), hair cells, hepatic cells, gastric mucosal cells, enterocytes, spleen cells, pancreatic cells (pancreatic exocrine cells and the like), brain cells, lung cells, kidney cells and skin cells.

(E) ES Cells Derived from Cloned Embryo Obtained by Nuclear Transfer ntES cells are ES cells derived from a cloned embryo obtained by the nuclear transfer technique, and have properties which are almost the same as those of ES cells derived from fertilized eggs (T. Wakayama et al. (2001), Science, 292:740-743; S. Wakayama et al. (2005), Biol. Reprod., 72:932-936; J. Byrne et al. (2007), Nature, 450:497-502). That is, an ntES (nuclear transfer ES) cell is an ES cell established from the inner cell mass of a blastocyst derived from a cloned embryo obtained by replacement of the nucleus of an unfertilized egg with the nucleus of a somatic cell. For preparation of an ntES cell, the combination of the nuclear transfer technique (J. B. Cibelli et al. (1998), Nature Biotechnol., 16:642-646) and the ES cell preparation technique (described above) is employed (Sayaka Wakayama et al. (2008), Experimental Medicine 26(5) (extra edition):47-52). In nuclear transfer, reprogramming can be achieved by injecting the nucleus of a somatic cell into a mammalian enucleated unfertilized egg and culturing the resultant for a several hours.

<Method of Differentiation Induction of Pluripotent Stem Cells>

In the present invention, "mesoderm" includes germ layers constituted by cells capable of producing, during development, the body cavity and mesothelium lining the body cavity, muscles, skeletons, dermis, connective tissues, heart/blood vessels (including vascular endothelium), blood (including blood cells), lymph vessels and spleen, kidney and ureter, and gonads (testis, uterus and gonadal epithelium). Mesodermal cells can be detected by expression of markers such as T (same as Brachyury), KDR, FOXF1, FLK1, BMP4, MOX1 and SDF1. Mesodermal cells preferably express T and KDR. In this invention, the mesodermal cells need not to be separated from other type of cell. The mesodermal cells can be contained with hematopoietic stem cells and/or hematopoietic progenitor cells.

In the present invention, "hematopoietic stem cells" means cells capable of producing mature blood cells such as T cells, B cells, erythrocytes, platelets, eosinophils, monocytes, neutrophils and basophils, which cells are also capable of self-renewal. Further, "hematopoietic progenitor cells" means cells which are differentiated from hematopoietic stem cells, whose direction of differentiation has been determined, and which are incapable of self-renewal. These cells can be detected by expression of markers such as KDR, CD34, CD90 and CD117, although the marker is not restricted.

In the method of the present invention for inducing differentiation of pluripotent stem cells into mesodermal cells, pluripotent stem cells are cultured in a serum-free medium without forming an embryoid body and without coculturing with cells from a different species.

Examples of "serum" include human serum, monkey serum, fetal calf serum, bovine serum, pig serum, equine serum, donkey serum, chicken serum, quail serum, sheep serum, goat serum, dog serum, cat serum, rabbit serum, rat serum, guinea pig serum and mouse serum, and culturing under "serum-free medium" means culturing in a medium which does not contain the serum. Preferably, the composition of the culture medium is clear. More preferably, the culturing may be carried out in a culture medium containing any one of albumin or an albumin alternative; transferrin or a transferrin alternative; insulin or an insulin alternative; and selenious acid. In the present invention, a preferred culture medium may be prepared by further adding cytokines to a basal medium. Examples of the basal medium which may be used include minimum essential medium (MEM), Dulbecco's modified Eagle's medium (DMEM), Iscove's modification of Dulbecco's medium (IMDM) and Stemline II Hematopoietic Stem Cell Expansion Medium (Stemline II). In the present invention, preferable medium is Stemline II containing insulin, transferrin and selenium. The Stemline II can be purchased from Sigma-Aldrich Corporation as product number, S0192. The insulin, transferrin and selenium mixture can be purchased from Sigma-Aldrich Corporation as ITS-X supplement.

In the aspect of efficiency of differentiation, the culture can be carried out at low oxygen condition. In the present invention, low oxygen condition is lower than 20%, preferably lower than 10%, more preferably lower than 5%, but not limited.

More preferably, in the method of the present invention, pluripotent stem cells are cultured to produce mesodermal cells in the following steps:

(1) pluripotent stem cells are cultured in the serum-free medium comprising BMP4; and (2) cells obtained in step (1) are cultured in the serum-free medium comprising VEGF.

Preferably, in the above method, the medium at step (2) further comprises SCF.

In another embodiment, in the above method, the medium at step (1) and (2) further comprises Wnt3a.

More preferably, the above method of producing mesodermal cells comprises in the following steps:

(i) pluripotent stem cells are cultured in the presence of BMP4 without Wnt3a;

(ii) cells obtained in step (i) are cultured in the presence of BMP4 and Wnt3a; and (iii) cells obtained in step (ii) are cultured in the presence of VEGF and Wnt3a;

The cells obtained after step (2) or (iii) contain, besides mesodermal cells, hematopoietic stem cells and/or hematopoietic progenitor cells in some amount. However, in order to induce differentiation of the mesodermal cells obtained in step (2) or (iii) into hematopoietic stem cells and/or hematopoietic progenitor cells, it is preferable that the mesodermal cells obtained in step (2) or (iii) are cultured in the presence of a hematopoietic factor(s) (step (3) or (iv)). The step (3) or (iv) is also preferable for inducing the differentiation of the mesodermal cells obtained in step (2) or (iii) into myeloid cells, megakaryocytes, erythrocytes and/or neutrophils.

"Hematopoietic factor" is a factor that promotes differentiation and growth of blood cells, and examples thereof include Stem Cell Factor (SCF), Colony-Stimulating Factor (CSF), Granulocyte-Colony Stimulating Factor (Granulocyte-(G-)CSF), Erythropoietin (EPO), interleukins, Thrombopoietin (TPO) and Flt3 ligand. Here, interleukins are proteins secreted from leukocytes, and can be divided into not less than 30 types such as IL-1, IL-2, IL-3, IL-4, IL-5, IL-6, IL-7, IL-8 and IL-9. Further, in the present invention, the interleukins may include a fusion protein between an IL-6 receptor and IL-6 (JP 2001-161350 A). In the present invention, preferable hematopoietic factors are selected from the group consisting of SCF, TPO, EPO, IL-3, Flt3-ligand, FP-6 and G-CSF. In the present invention, the hematopoietic factors are more preferably the combination of SCF, TPO, IL-3, Flt3-ligand and G-CSF; or the combination of SCF, TPO, IL-3, FP-6 and EPO; or the combination of SCF, IL-3, and G-CSF.

The concentration of each cytokine to be added to the culture medium is not restricted as long as the cells of interest can be obtained therewith, and, in the case of BMP4, the concentration may be 5 ng/ml to 50 ng/ml, preferably 20 ng/ml to 40 ng/ml. In the case of Wnt3a, the concentration may be 5 ng/ml to 50 ng/ml, preferably 10 ng/ml to 20 ng/ml. In the case of VEGF, the concentration may be 5 ng/ml to 50 ng/ml, preferably 10 ng/ml to 20 ng/ml. In the case of SCF, the concentration is 20 ng/ml to 100 ng/ml, preferably 50 ng/ml. In the case of IL-3, the concentration is 5 ng/ml to 50 ng/ml, preferably 10 ng/ml. In the case of TPO, the concentration is 5 ng/ml to 50 ng/ml, preferably 5 ng/ml. In the case of Flt3-ligand, the concentration is 10 ng/ml to 200 ng/ml, preferably 50 ng/ml. In the case of G-CSF, the concentration is 20 ng/ml to 100 ng/ml, preferably 50 ng/ml. In the case of FP-6, the concentration is 20 ng/ml to 100 ng/ml, preferably 50 ng/ml. In the case of EPO, the concentration is 1 IU/ml to 20 IU/ml, preferably 2.5 IU/ml.

The period of culturing in the presence of the cytokine or combination of cytokines is, in the above case of "the step (1)", more than 2 day, preferably 4 days or more, more preferably 4 days. In the above case of "the step (2)", the period of culturing is more than 2 days, preferably 2 days. In the above case of "the step (i)", the period of culturing is not less than 1 day, preferably 1 to 6 days, more preferably about 1 day. In the above case of "the step (ii)", the period of culturing is not less than 2 days, preferably 2 to 8 days, more preferably about 3 days. In the above case of "the step (iii)", the period of culturing is not less than 1 day, preferably 1 to 6 days, more preferably about 2 days. In the case of "(4) hematopoietic factors", the period of culturing is not less than 5 days, and preferably longer in order to further produce myeloid cells, megakaryocytes and/or erythrocytes from the obtained mesodermal cells.

"Embryoid body" is a cell mass having an embryo-like shape observed during suspension culture of pluripotent stem cells, and especially a structure which is induced from a cell other than a fertilized egg and which follows morphogenesis very similar to embryogenesis from a fertilized egg. The culture condition of "without formation of an embryoid body" more particularly means adherent culture. In the adherent culture of the present invention, the culture dish may be preliminarily coated with gelatin, hyaluronic acid, laminin, collagen, proteoglycan, fibronectin, entactin, or the like before allowing the cells to adhere thereto, and a culture dish coated with Growth factor-reduced Matrigel™ (BD Biosciences) is preferably used.

"Cells from a different species" means cells derived from a species different from the animal species from which the pluripotent stem cells were derived, and preferably means cells other than the pluripotent stem cells of interest. In the case of using human pluripotent stem cells, the cells from a different species are non-human cells.

The production method of the present invention aims to provide production of mesodermal cells, and cells produced by the method may be partially constituted by mesodermal cells, and may contain other cells such as mesodermal progenitor cells, mesendoderm cells, hematopoietic stem cells and/or hematopoietic progenitor cells, myeloid cells, megakaryoblasts, platelets, granulocytes, erythroblasts, erythrocytes, vascular endothelial cells and/or vascular endothelial progenitor cells.

In the present invention, "myeloid Cells" means cells capable of producing eosinophils, monocytes, neutrophils and basophils. These cells can be detected by expression of markers such as CD45, CD19, CD13 CD33 and MPO, although the marker is not restricted.

In the present invention, "megakaryocytes" means cells capable of producing platelet. These cells can be detected by expression of markers such as CD41a, 41b and 42b, although the marker is not restricted.

In the present invention, "erythrocytes" is rich in hemoglobin and can be detected by expression of markers such as α-globin, ε-globin, γ-globin and β-globin of hemoglobin, although the marker is not restricted. In the aspect of mature erythrocyte, preferably markers are α-globin and β-globin.

In the present invention, "neutrophils" can be detected by expression of markers such as CD16 (Fc-gamma-RIIIB), although the marker is not restricted.

EXAMPLES

The present invention will now be described more concretely by way of Examples below, but the scope of the present invention is not limited to the Examples.
Cells and Culturing Human ES cells (KhES-1 and KhES-3) were received from Institute for Frontier Medical Sciences, Kyoto University, and cultured by a conventional method (Suemori H, et al. Biochem Biophys Res Commun. 345:926-32, 2006). Human iPS cells (253G1(G1), 253G4(G4), 207B6(B6) and 207B7 (B7)) were received from Prof. Yamanaka at Kyoto University and cultured by a conventional method (Takahashi K, et al. Cell. 131:861-72, 2007; Nakagawa M, et al. Nat Biotechnol. 26:101-6, 2008).

Example 1

Figure 2:
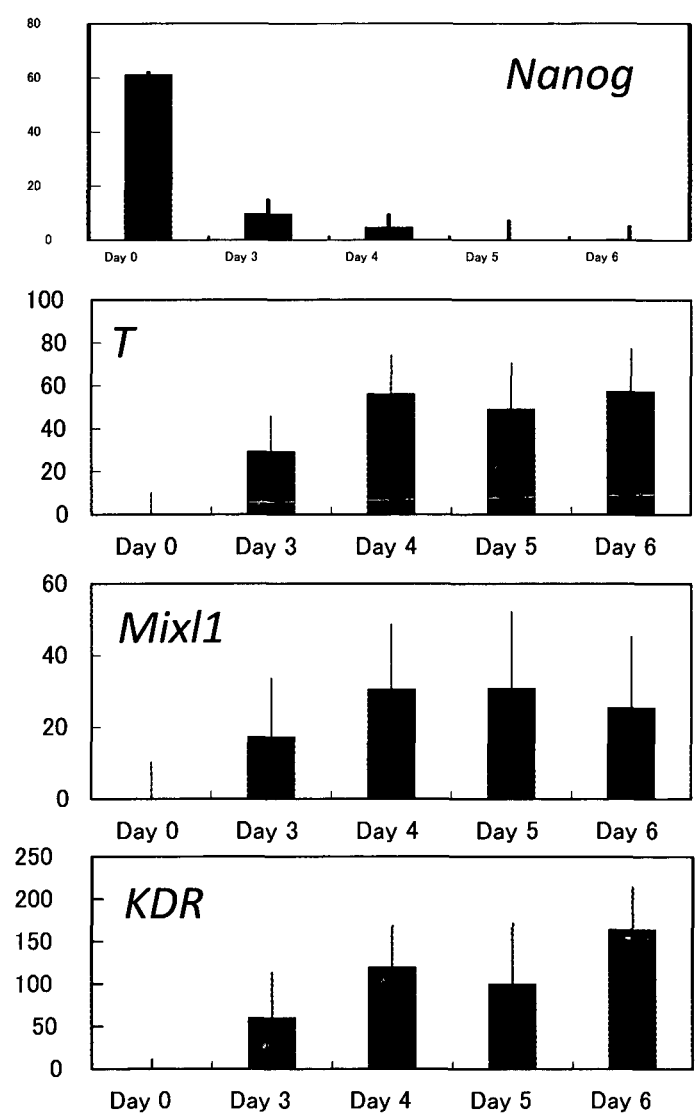
FIG. 2 shows the results of quantitative PCR for the respective markers on Day 0, Day 3, Day 4, Day 5 and Day 6 after the beginning of the differentiation induction.

Differentiation Induction into Mesoderm Containing Hematopoietic Stem Cells and/or Hematopoietic Progenitor Cells By the schemes of Step A and Step B described in FIG. 1A, mesoderm containing hematopoietic stem cells and/or hematopoietic progenitor cells was prepared. Briefly, KhES-3 which had been maintained in an undifferentiated state was cultured for 1 day in a Growth factor-reduced Matrigel (BD Biosciences)-coated dish containing a culture medium prepared by adding ITS-X (Gibco) to Stemline II (S0192, Sigma) and further adding 20 ng/ml BMP4 thereto. This was followed by culturing for additional 3 days in the medium to which 10 ng/ml Wnt3a was further added. Subsequently, the medium was replaced with a medium prepared by adding ITS-X to Stemline II and further adding 10 ng/ml Wnt3a and 10 ng/ml VEGF thereto, and the cells were then cultured for 2 days. Gene expression was analyzed in the obtained cells and as a result, expression of mesodermal markers T and KDR and an embryonic endodermal marker Mixl1 was confirmed (FIG. 1B and FIG. 2). Further, at this time, disappearance of expression of undifferentiation markers Oct3/4 and Nanog was also confirmed.

Figure 3:
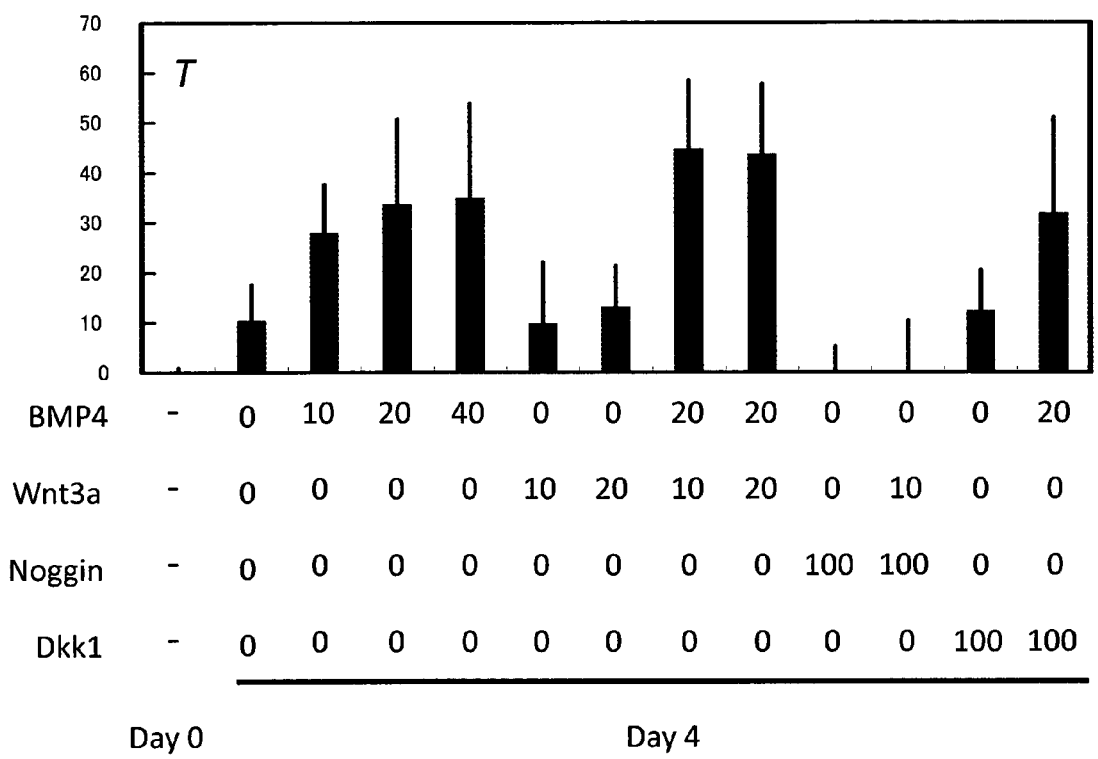
FIG. 3 shows the results obtained by measuring with quantitative PCR, the expression levels of T under the respective conditions with or without the various amounts of BMP4, Wnt3a, Noggin (BMP4 inhibitor) and DKK1 (Wnt3a inhibitor). The concentrations (ng/mL) of the respective additives are shown under the graph.

The optimum concentrations of BMP4 and Wnt3a were studied by evaluating with expression of T as an index, and the concentration of BMP4 was confirmed to be preferably not less than 20 ng/ml. Similarly, the concentration of Wnt3a was confirmed to be preferably not less than 10 ng/ml (FIG. 3). Since addition of a BMP4 inhibitor Noggin caused disappearance of expression of T, it was confirmed that BMP4 is essential for the differentiation induction.

Figure 4:
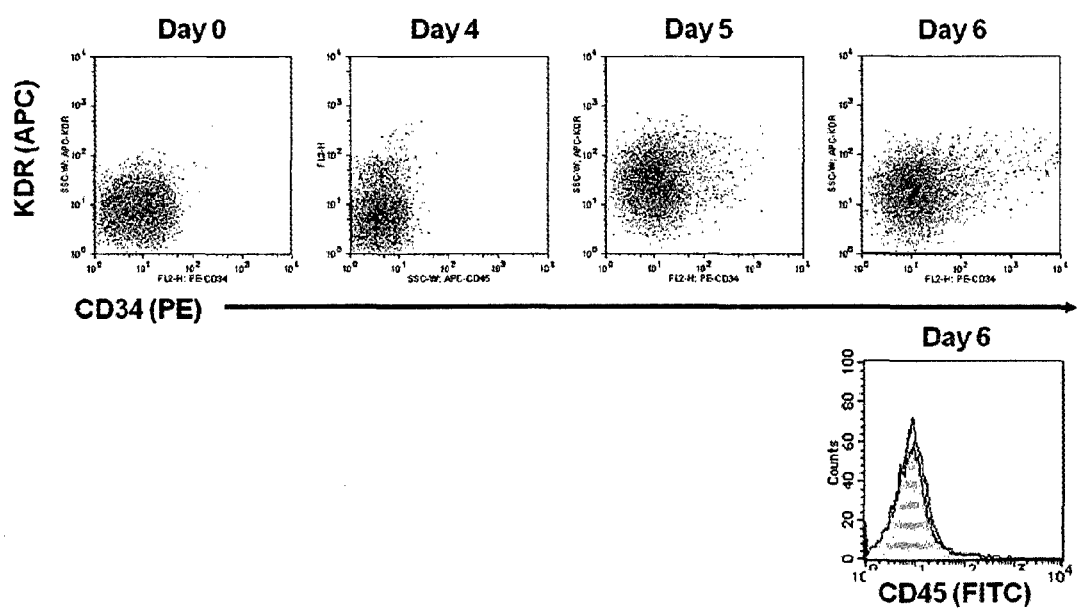
FIG. 4 shows the results of flow cytometry for detection of KDR and CD34 on Day 0, Day 3, Day 4, Day 5 and Day 6 after the beginning the differentiation induction (the upper panels), and CD45 on Day 6 (the lower panel).
Figure 5:
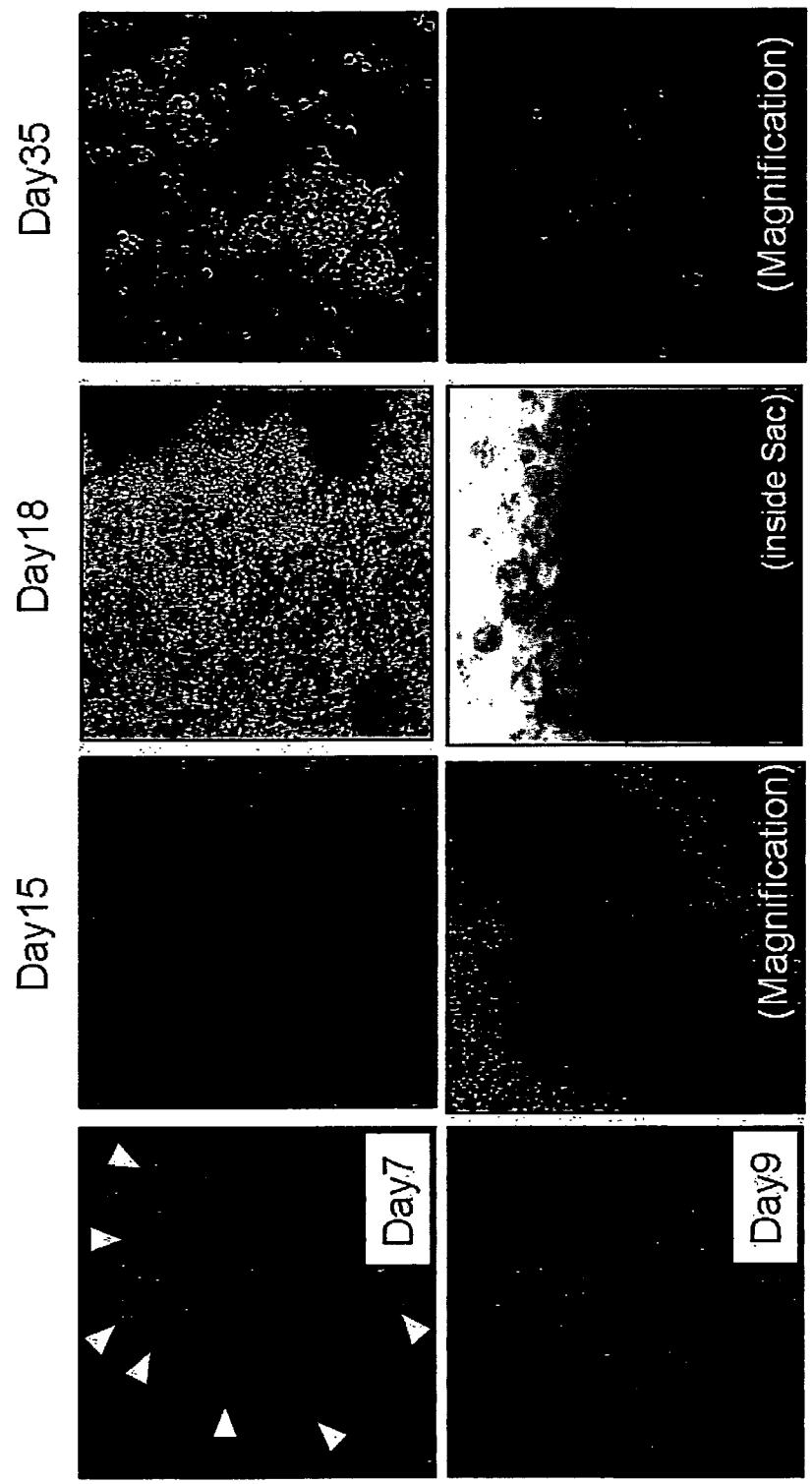
FIG. 5 shows phase contrast micrographs (photograph) taken on Day 7, Day 9, Day 15, Day 18 and Day 35 after the beginning of the differentiation induction. In each of the results for Day 15, Day 18 and Day 35, the lower panel shows a magnified image of the upper panel.

Subsequently, changes in the cells on the respective days during the differentiation induction were studied using a flow cytometer, and it was confirmed that the mesoderm obtained by the differentiation induction contains KDR-positive CD34-positive CD45-negative cells (FIG. 4). Thus, it was confirmed that, by using the present method of differentiation induction, mesoderm containing hematopoietic stem cells and/or hematopoietic progenitor cells can be induced.
Differentiation Induction into Myeloid Cells, Megakaryocytes and Erythroblasts The mesoderm obtained by the above method was subjected to differentiation induction using a myeloid inducing factor cocktail (Cocktail A: 50 ng/mL SCF (R&D Systems), 5 ng/mL TPO (Kyowa Hakko Kirin Co., Ltd.), 50 ng/mL IL-3 (R&D Systems), 50 ng/mL Flt3-ligand (R&D Systems) and 50 ng/mL G-CSF (Kyowa Hakko Kirin Co., Ltd.)) or a megakaryoblast/erythroblast inducing factor cocktail (Cocktail B: 50 ng/mL SCF, 5 ng/mL TPO, 50 ng/mL IL-3, 50 ng/mL FP-6 (Kyowa Hakko Kirin Co., Ltd.) and 2.5 IU/mL EPO (Kyowa Hakko Kirin Co., Ltd.)), while replacing the culture medium every 5 days, as in Step C described in FIG. 1A. As a result, a sac-like structure appeared outside the colony from Day 8 (FIG. 5). Subsequently, on Day 12 to Day 15, floating hemocyte-like cells were confirmed.

Figure 6:
In FIG. 6, A shows stained images (photograph) of the cells cultured for 24 days after replacement of the culture medium with a myeloid inducing factor cocktail (Cocktail A) or a megakaryoblast/erythroblast inducing factor cocktail (Cocktail B), which replacement was carried out on Day 6 after the beginning of the differentiation induction. The upper panels show images obtained by May-Giemsa staining and the lower panels show images obtained by MPO staining. The center and right panels show immunostained images for hHb and CD41, respectively. "Ery" indicates an erythrocyte, and "Mk" indicates a megakaryocyte.
Figure 6:
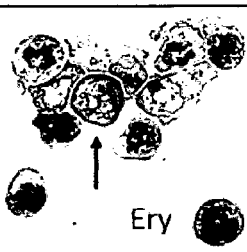
Figure 6:
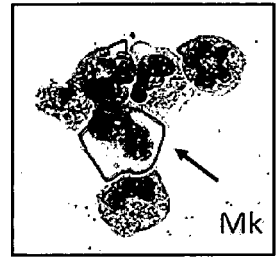
Figure 6:
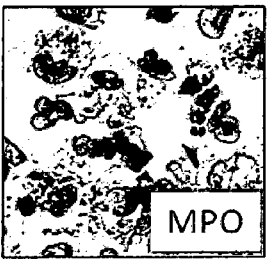
Figure 6:
Figure 6:
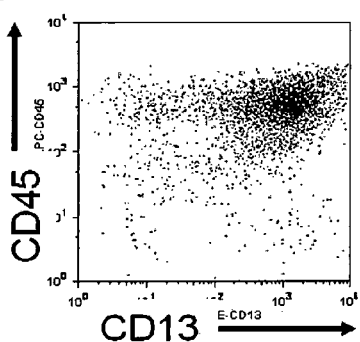
Figure 6:
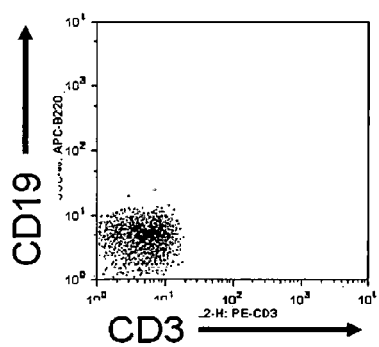
Figure 6:
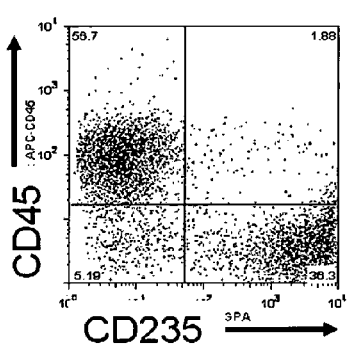

In order to investigate the cell lineages of these hemocyte-like cells, the cells after 30 days of the differentiation induction using the myeloid inducing factor cocktail or megakaryoblast/erythroblast inducing factor cocktail were subjected to May-Giemsa staining, MPO (myeloperoxidase) staining and immunostaining (FIG. 6A). As a result, it was revealed that, in cases where the myeloid inducing factor cocktail was used, most of the cells belonged to the myelomonocytic cell lineage and a part of the cells were MPO staining-positive cells. On the other hand, in cases where the megakaryoblast/erythroblast inducing factor cocktail was used, the cells were induced to differentiate into not only the myelomonocytic cell lineage, but also various blood cell lineages including hemoglobin-positive erythrocytes and CD41-positive megakaryoblasts.

Figure 7:
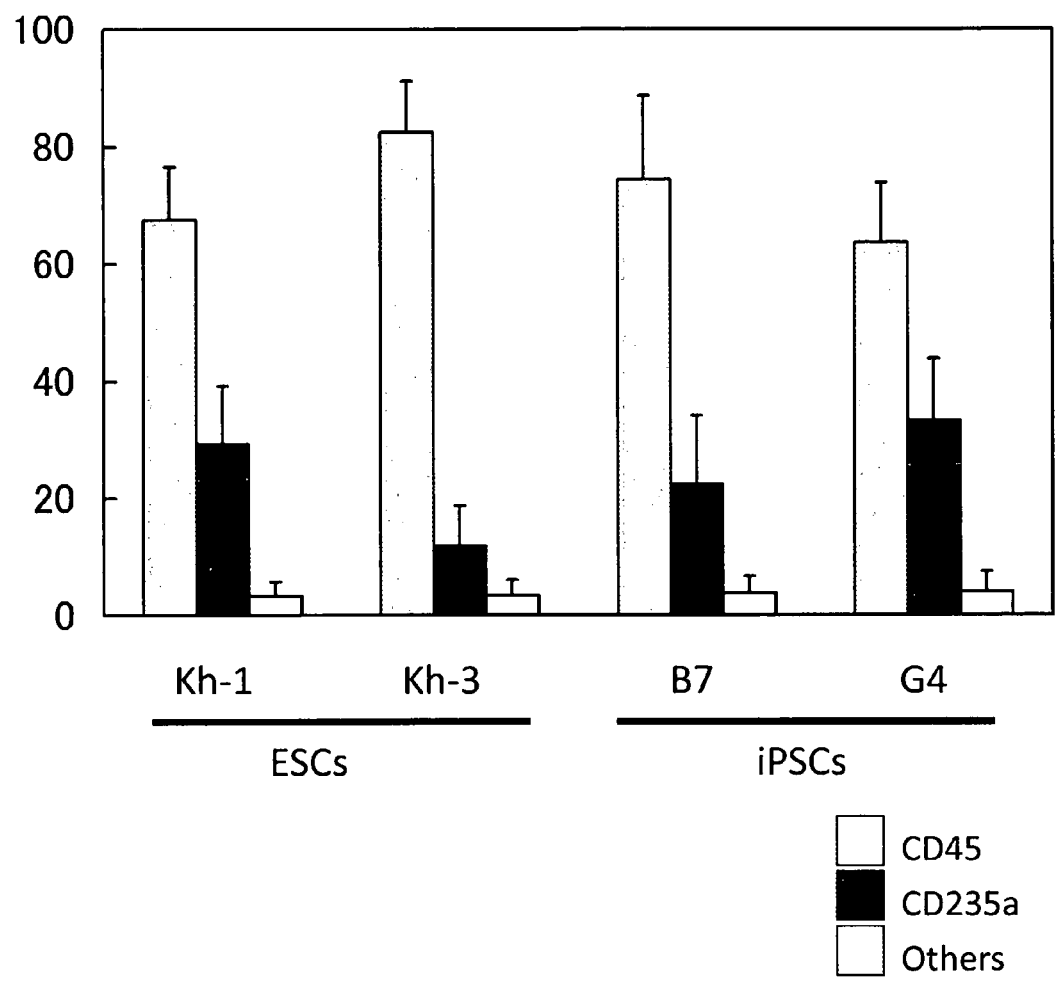
FIG. 7 shows the results of flow cytometry for detection of cells expressing the respective marker proteins on Day 30 after the beginning of the differentiation induction of the respective pluripotent stem cells (Kh-1 and Kh-3: ES cells; B7 and G4: iPS cells) with the megakaryoblast/erythroblast inducing factor cocktail.
Figure 8:
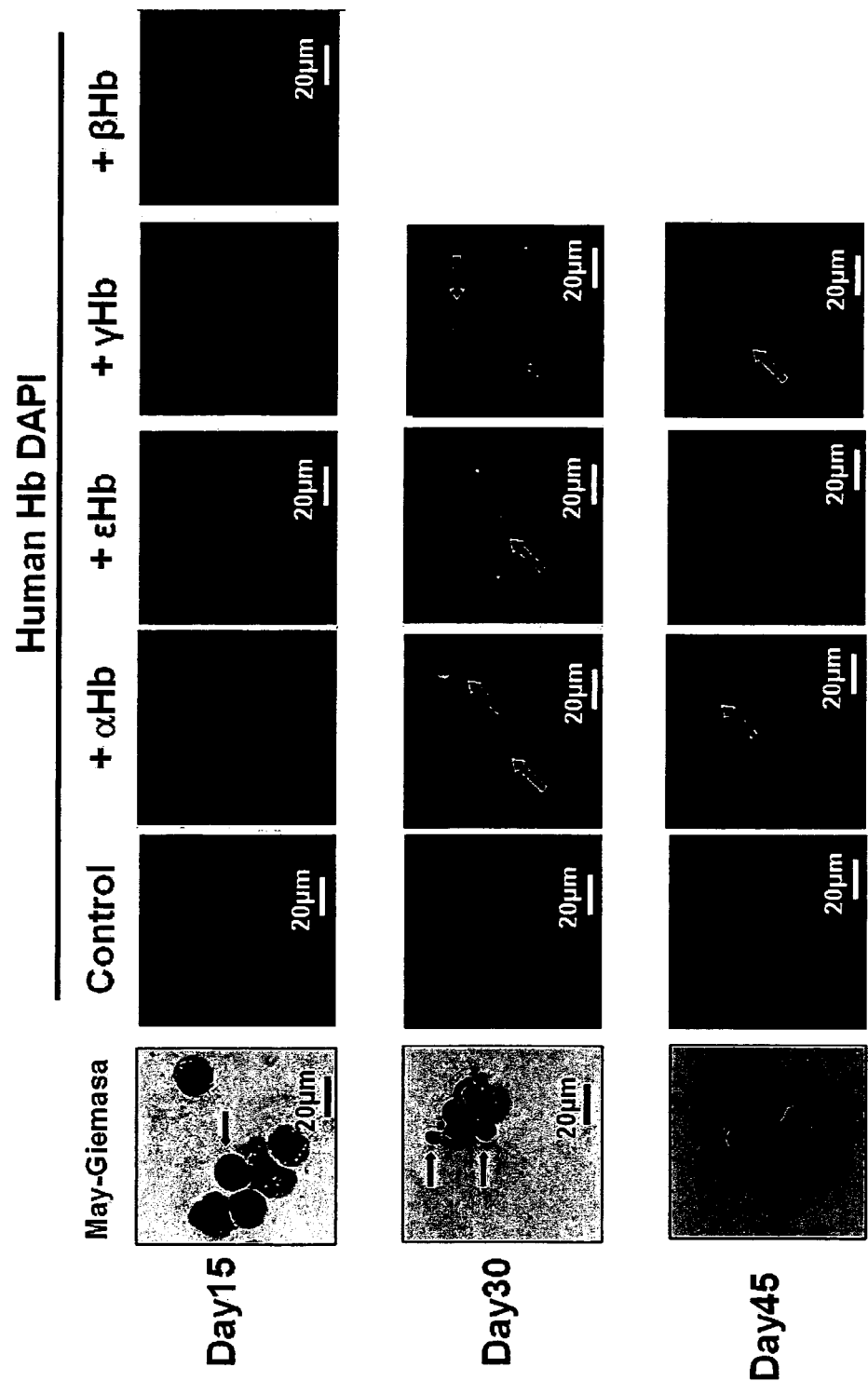
FIG. 8 shows images (photograph) obtained by staining α-globin (αHb), ε-globin (εHb), γ-globin (γHb) and β-globin (βHb) of hemoglobin, which were taken on Day 15, Day 30 and Day 45 after the beginning of the differentiation induction using Cocktail B.
Figure 9:
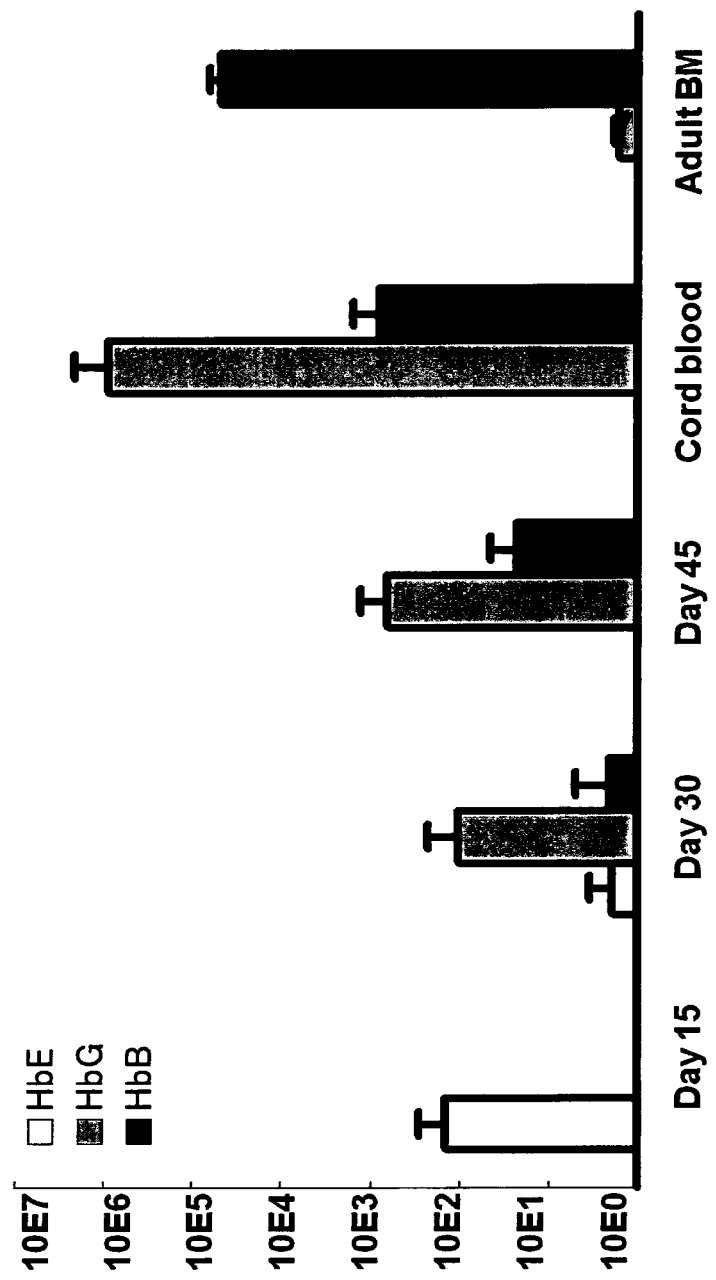
FIG. 9 shows the numbers of cells positive for ε-globin (εHb), γ-globin (γHb) and β-globin (βHb) on the respective days in the differentiation-induced cells and in cord blood and adult bone marrow (Adult BM) cells a control cells.

Subsequently, the lineages of the cells after 30 days of the differentiation induction was investigated in detail by flow cytometry. In cases where the myeloid inducing factor cocktail was used, most of the cells belonged to the CD13-positive CD45-positive myelomonocytic cell lineage (FIG. 6B). On the other hand, in cases where the megakaryoblast/erythroblast inducing factor cocktail was used, the cells belonged to the CD235 (Glycophorin A)-positive and/or CD45-positive myelomonocytic cell lineage. The differentiation induction into these cell lineages occurred irrespective of the types of the cell lines of ES cells and iPS cells, and almost the same results were obtained for all the cell lines after 30 days of differentiation induction using the megakaryoblast/erythroblast inducing factor cocktail (FIG. 7).
Differentiation Induction into Erythrocytes The floating erythrocyte-like cells obtained by the differentiation induction using the megakaryoblast/erythroblast inducing factor cocktail were investigated in detail using May-Giemsa staining and immunostaining (FIG. 8 and FIG. 9). Fifteen days of the differentiation induction resulted in nucleated ε-globin-positive cells. On the other hand, after 30 days of the differentiation induction, the sizes of the cells clearly decreased, and enucleated cells were partially observed. At this time, ε-globin-positive cells decreased, and γ-globin- and β-globin-positive cells appeared. Further, after 45 days of the differentiation induction, enucleated cells could be often seen, and α-globin- and β-globin-positive cells appeared. Thus, by the present method of differentiation induction, stepwise induction from hematopoietic progenitor cells into erythrocytes was possible.

Figure 10:
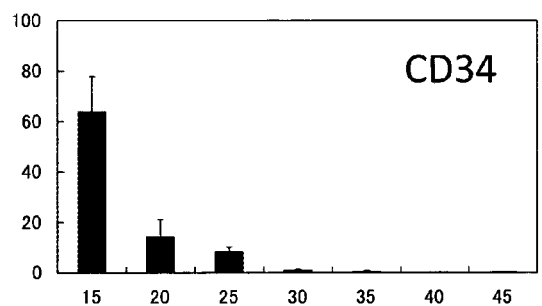
FIG. 10 shows the contents of CD34- and CD117-positive cells on the respective days after the beginning of the differentiation induction.
Figure 10:
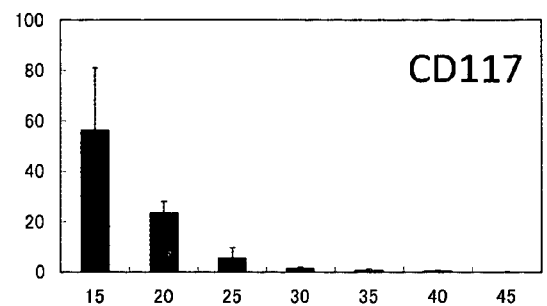

Differentiation Induction into Hematopoietic Stem Cells and/or Hematopoietic Progenitor Cells In order to confirm the fact that hematopoietic stem cells and/or hematopoietic progenitor cells were obtained by the differentiation induction using the megakaryoblast/erythroblast inducing factor cocktail as described above, expression of CD34 and CD117 (c-Kit) was investigated by flow cytometry (FIG. 10). On Day 15 of the differentiation induction, there were many cells expressing the both markers, and cells expressing these two markers existed until Day 25 of the differentiation induction, so that it was confirmed that immature hematopoietic cells were cultured.

Figure 11:
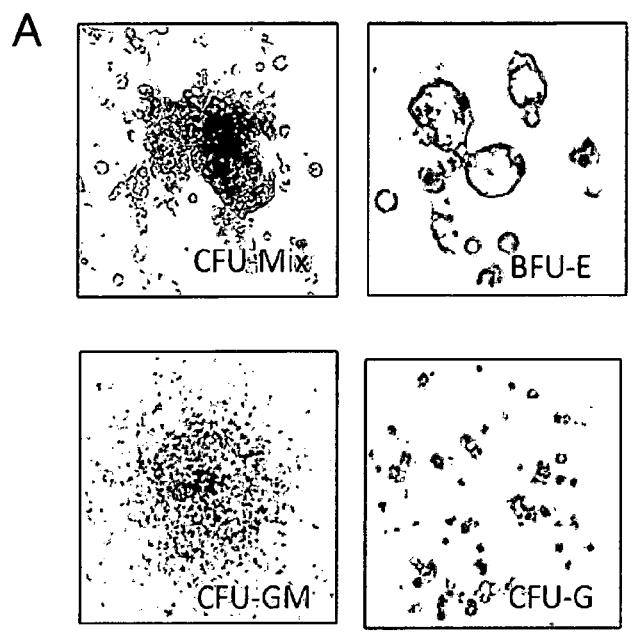
In FIG. 11, A shows representative phase contrast micrographs (photograph) of the respective colonies in the colony formation assay. CFU-Mix, BFU-E, CFU-GM and CFU-G indicate a mixed colony-forming unit, burst-forming unit erythroid, colony-forming units granulocyte-monocyte and colony-forming units granulocyte, respectively.
Figure 11:
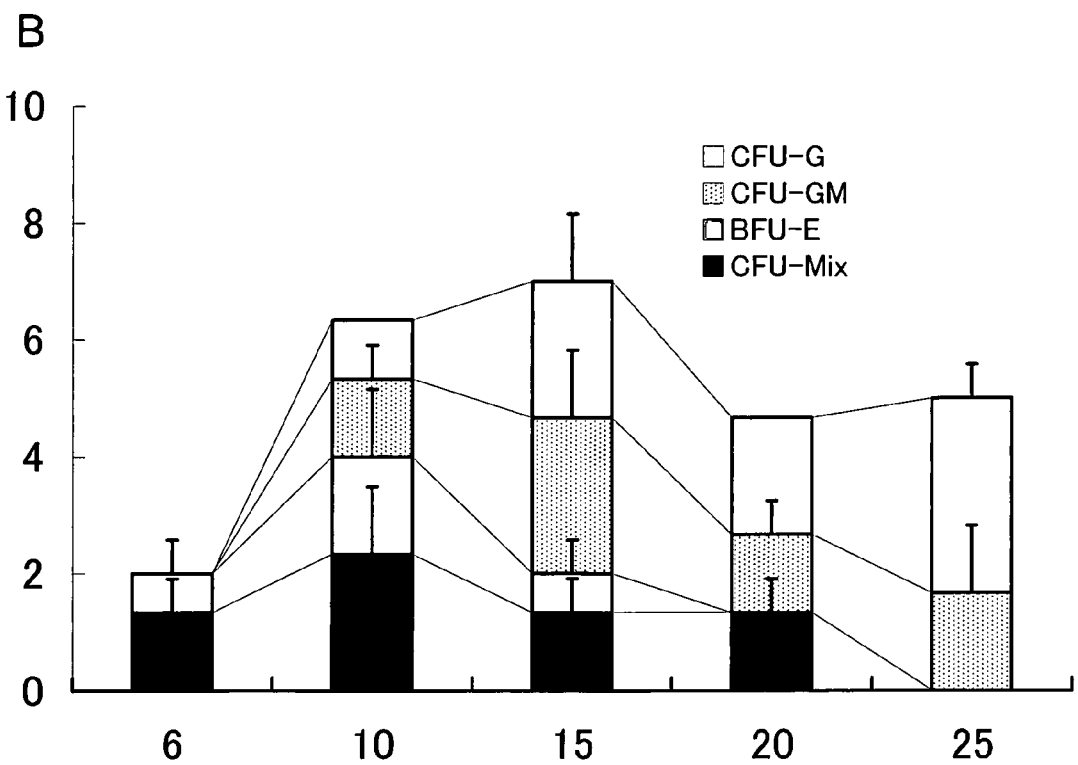

Using methylcellulose medium containing SCF, TPO, IL3, G-CSF and EPO, a colony formation assay was carried out with the cells obtained by the differentiation induction. Representative CFU-Mix, BFU-E, CFU-GM and CFU-G are shown in FIG. 11A. Further, changes in formation of these colonies with time are shown in FIG. 11B. The numbers of the colonies increased until Day 8 to Day 10, and decreased thereafter. Further, CFU-Mix, BFU-E and CFU-M were found until Day 15, but gradually changed into CFU-GM and CFU-G.

Figure 12:
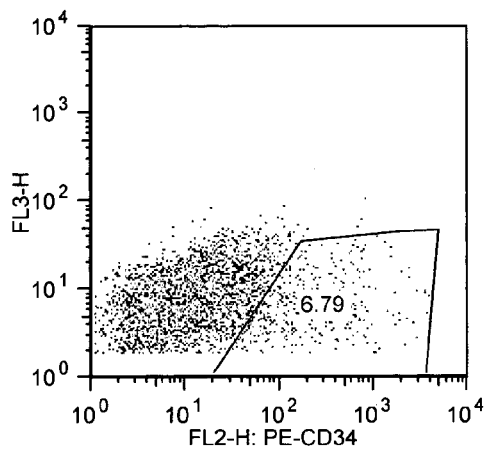
FIG. 12 shows the results of flow cytometry wherein expression of CD34, CD38 and CD90 was confirmed on Day 20 after the beginning of the differentiation induction.
Figure 12:
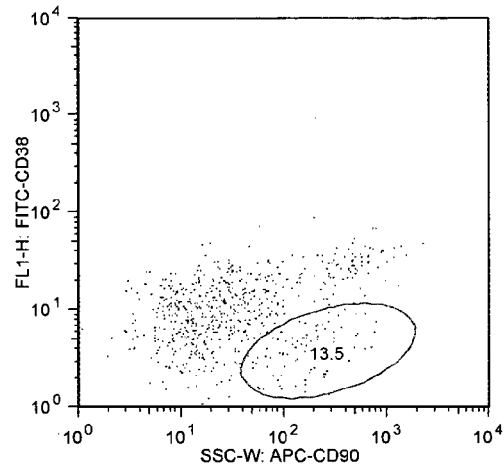

Further, expression of CD34, CD90 and CD38 in the cells after 20 days of the differentiation induction using the megakaryoblast/erythroblast inducing factor cocktail was confirmed using a flow cytometer, and it was revealed that these cells were CD34-positive, CD90-positive and CD38-negative (FIG. 12).

Thus, based on the fact that many types of cell lineages are induced by continuing the differentiation induction, and on the expression patterns of the respective markers, it was confirmed that hematopoietic stem cells and/or hematopoietic progenitor cells were obtained by using the present method of differentiation induction.

Figure 13:
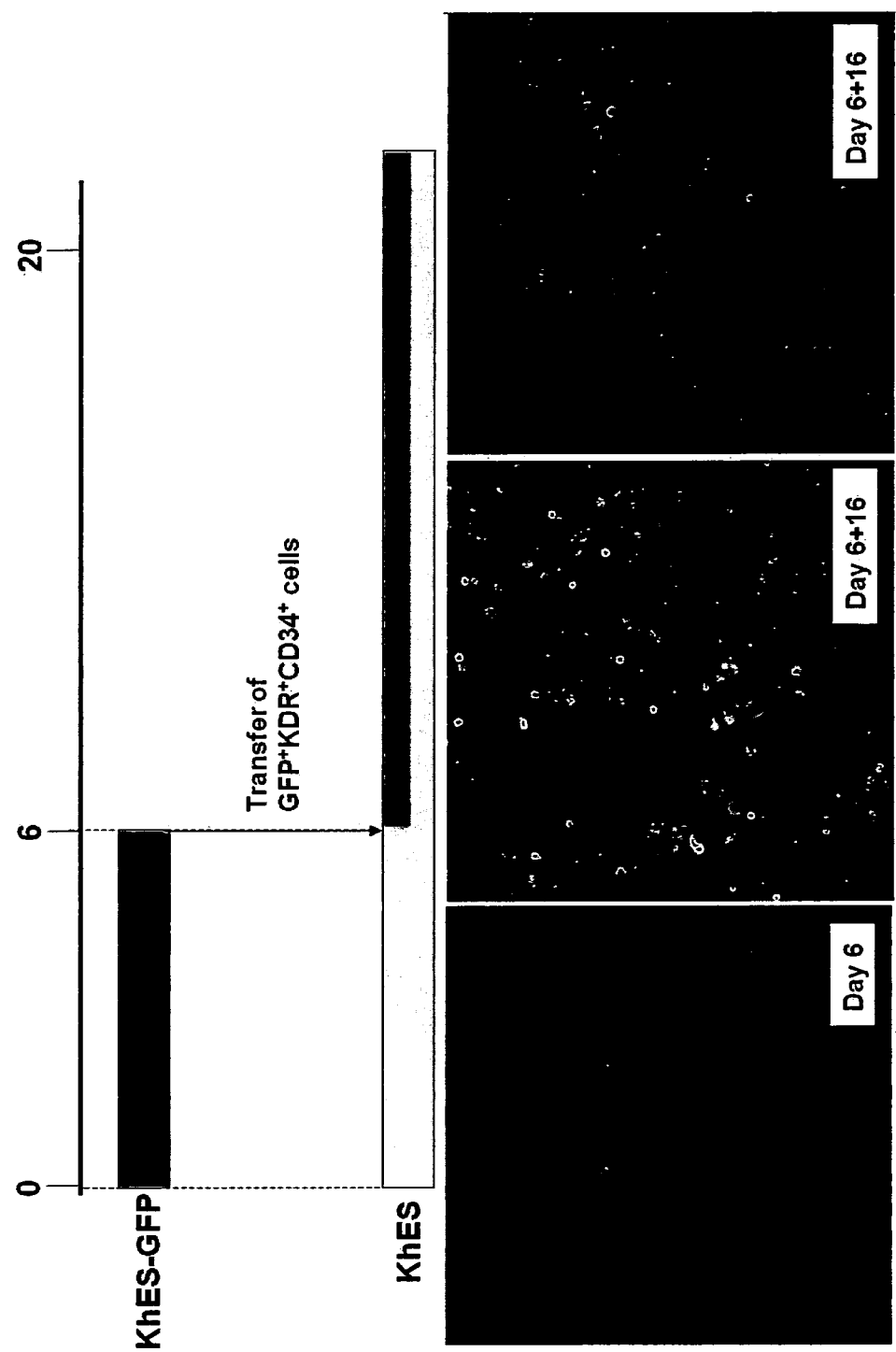
FIG. 13 shows a scheme wherein GFP-positive ES cells and normal ES cells are mixed together after the differentiation induction, and fluorescence micrographs (photograph) taken on Day 6 and Day 22 after the beginning of the differentiation induction.

Subsequently, in order to confirm that the KDR-positive CD34-positive cells existing on Day 6, Day 8 and Day 10 of the differentiation induction directly differentiate into CD45-positive cells or endothelial cells, KDR-positive CD34-positive cells, KDR-positive CD34-negative cells and KDR-negative cells which were derived from KhES-3 and forced to express GFP were cultured on cells prepared by allowing differentiation of GFP-nonexpressing KhES in the same manner, while tracing the GFP-positive cells, thereby investigating which fraction of the cells differentiate more easily into mesodermal cells or mesodermal progenitor cells under the environment during the differentiation from ES cells (FIG. 13). As a result, differentiation induction into blood cells or endothelial cells was more frequently observed in the cells expressing KDR. Therefore, it was confirmed that the KDR-positive cells produced by differentiation induction by the present method contain mesodermal progenitor cells having hematopoietic activity.

Example 2

Figure 14:
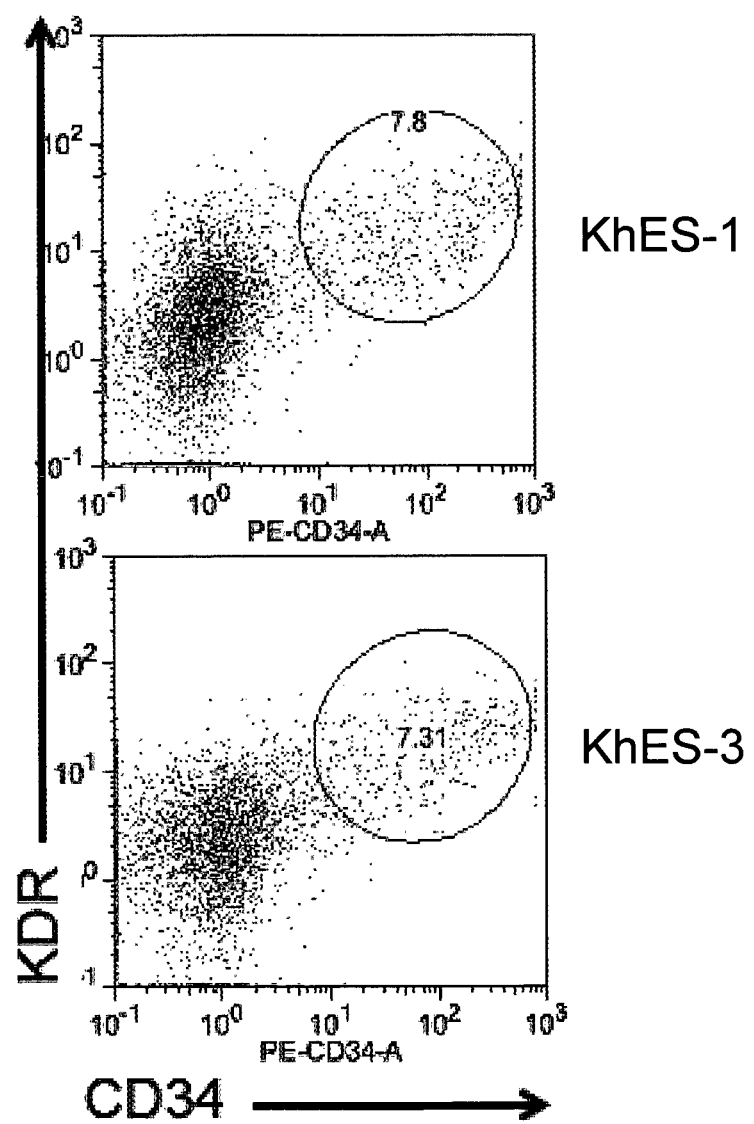
FIG. 14 shows the results of flow cytometry for detection of expression of KDR and CD34 in the cells cultured for 2 days after replacement of the culture medium with BMP4, which replacement was carried out on Day 4 after the differentiation induction using the culture medium with VEGF.

Differentiation Induction into Mesoderm Containing Hematopoietic Stem Cells and/or Hematopoietic Progenitor Cells KhES-1 or KhES-3, which had been maintained in an undifferentiated state for 2 days in a Growth factor-reduced Matrigel-coated dish, was cultured at 5% $O_2$ condition for 4 days in a culture medium prepared by adding ITS-X to Stemline II and further adding 20 ng/ml BMP4 thereto. After that, the culture medium was changed to Stemline II with the addition of ITS-X, 40 ng/ml VEGF and 50 ng/ml SCF, and these cells were cultured for 2 days at 5% $O_2$ condition. Then, KDR and CD34 positive cells were confirmed by flow cytometry analysis (FIG. 14). Thus, it was confirmed that, by using the present method of differentiation induction, mesoderm containing hematopoietic stem cells and/or hematopoietic progenitor cells can be induced.

Differentiation Induction into Neutrophil

The mesoderm cells obtained by the above method were subjected to differentiation induction using Stemline II with the addition of ITS-X, 50 ng/ml SCF, 50 ng/ml IL-3, 50 ng/ml G-CSF, while replacing the culture medium every 4 or 5 days. After 9 days, the cells were induced to differentiate into neutrophils.

INDUSTRIAL APPLICABILITY

By the present invention, mesodermal cells can be prepared from pluripotent stem cells such as ES cells and iPS cells. The obtained mesodermal cells can be efficiently differentiated into various types of cell including hematopoietic stem cells and/or hematopoietic progenitor cells. The hematopoietic stem cells and/or hematopoietic progenitor cells can be used in the field of regenerative medicine for therapy of leukemia, anaplastic anemia and the like.

The invention claimed is:

1. A method for producing mesodermal cells comprising:
   a) culturing pluripotent stem cells under adherent conditions and without co-culture with cells from a different species in a serum-free medium comprising BMP4 without Wnt3a;
   b) culture the cells of step (a) under adherent conditions and without co-culture with cells from a different species in a serum-free medium comprising BMP4 and Wnt3a; and
   c) culturing the cells of step (b) under adherent conditions and without co-culture with cells from a different species in a serum-free medium comprising VEGF and Wnt3a,
   thereby producing mesodermal cells containing hematopoietic stem cells and/or hematopoietic progenitor cells.

2. The method according to claim 1, wherein the serum-free medium at step (3) further comprises SCF.

3. The method according to claim 1, wherein the cells in steps (a), (b) and (c) are cultured on a Matrigel™ coating dish.

4. The method according to claim 1, wherein the step (a) is performed for 1 day.

5. The method according to claim 1, wherein the step (b) is performed for 3 days.

6. The method according to claim 1, wherein the step (c) is performed for 2 days.

7. The method according to claim 1, wherein said mesodermal cells contain KDR-positive and CD34-positive cells.

8. A method for producing hematopoietic stem cells, hematopoietic progenitor cells, myeloid cells, megakaryocytes, erythrocytes and/or neutrophils, comprising:
   a) culturing pluripotent stem cells under adherent conditions and without co-culture with cells from a different species in a serum-free medium comprising BMP4 without Wnt3a;
   b) culture the cells of step (a) under adherent conditions and without co-culture with cells from a different species in a serum-free medium comprising BMP4 and Wnt3a; and
   c) culturing the cells of step (b) under adherent conditions and without co-culture with cells from a different species in a serum-free medium comprising VEGF and Wt3a, d) culturing the mesodermal cells obtained in step (c) in the presence of a hematopoietic factor(s) selected from the group consisting of SCF, TPO, EPO, IL-3, Flt3-ligand, FP-6 and G-CSF, thereby producing hematopoietic stem cells, hematopoietic progenitor cells, myeloid cells, megakaryocytes, erythrocytes and/or neutrophils.

9. The method according to claim 8, wherein the step (b) is performed for 9 days or more.

* * * * *

UNITED STATES PATENT AND TRADEMARK OFFICE
CERTIFICATE OF CORRECTION

PATENT NO. : 8,652,845 B2  
APPLICATION NO. : 13/635679  
DATED : February 18, 2014  
INVENTOR(S) : Akira Niwa Page 1 of 1

It is certified that error appears in the above-identified patent and that said Letters Patent is hereby corrected as shown below:

In the Specification

In column 9 at line 41, Change "Wnt3a;" to --Wnt3a.--.

In the Claims

In column 14 at line 31, In Claim 1, change "b) culture" to --b) culturing--.

In column 14 at line 60, In Claim 8, change "b) culture" to --b) culturing--.

In column 14 at line 63, In Claim 8, after "Wnt3a;" delete "and".

In column 14 at line 67, In Claim 8, change "Wt3a" to --Wnt3a; and--.

In column 15 at line 8, In Claim 9, change "step (b)" to --step (d)--.

Signed and Sealed this  
Ninth Day of December, 2014

Michelle K. Lee  
*Deputy Director of the United States Patent and Trademark Office*